(12) United States Patent
Okuno et al.

(10) Patent No.: US 12,369,872 B2
(45) Date of Patent: Jul. 29, 2025

(54) RADIOGRAPHIC IMAGING DEVICE

(71) Applicant: Shimadzu Corporation, Kyoto (JP)

(72) Inventors: Tomoharu Okuno, Kyoto (JP); Hideki Fujii, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 846 days.

(21) Appl. No.: 17/272,583

(22) PCT Filed: Sep. 26, 2018

(86) PCT No.: PCT/JP2018/035680
§ 371 (c)(1),
(2) Date: Mar. 1, 2021

(87) PCT Pub. No.: WO2020/065761
PCT Pub. Date: Apr. 2, 2020

(65) Prior Publication Data
US 2021/0378614 A1    Dec. 9, 2021

(51) Int. Cl.
*A61B 6/46* (2024.01)
*A61B 6/00* (2024.01)
*A61B 6/58* (2024.01)

(52) U.S. Cl.
CPC ............ *A61B 6/467* (2013.01); *A61B 6/465* (2013.01); *A61B 6/54* (2013.01); *A61B 6/58* (2013.01)

(58) Field of Classification Search
CPC .......... A61B 6/467; A61B 6/465; A61B 6/54; A61B 6/58
See application file for complete search history.

(56) References Cited

U.S. PATENT DOCUMENTS

| | | | |
|---|---|---|---|
| 8,041,001 B2 * | 10/2011 | Hirota | G16Z 99/00 600/407 |
| 11,399,785 B2 * | 8/2022 | Ohara | A61B 6/527 |

(Continued)

FOREIGN PATENT DOCUMENTS

| | | |
|---|---|---|
| CN | 101653363 A | 2/2010 |
| JP | 2000-325339 A | 11/2000 |

(Continued)

OTHER PUBLICATIONS

Written Opinion by the International Search Authority for PCT application No. PCT/JP2018/035680, dated Dec. 18, 2018, submitted with a machine translation.

(Continued)

*Primary Examiner* — Carolyn Fin
(74) *Attorney, Agent, or Firm* — Muir Patent Law, PLLC

(57) ABSTRACT

After an operator presses a practice mode execution start switch displayed on a touch panel liquid crystal display unit in an operation unit (2) or a touch panel liquid crystal display unit in an operation unit (41) to shift an imaging mode to a practice mode, when the operation unit (2) or the operation unit (41) of the imaging unit is operated, the signal from the X-ray imaging control unit (72) is transmitted to the voice guidance output control unit (52) in a voice guidance unit (5) via a signal output unit for a voice guidance unit (73). The voice guidance output control unit (52) in the voice guidance unit (5) transmits a signal for outputting voice guidance to a speaker (51). As a result, the same voice as a voice when performing the serial imaging is output from the speaker (51). Thus, a subject can execute the practice of a breathing method or the like.

5 Claims, 7 Drawing Sheets

(56) References Cited

U.S. PATENT DOCUMENTS

| | | | |
|---|---|---|---|
| 2005/0244044 A1 | 11/2005 | Inoue | |
| 2008/0089463 A1* | 4/2008 | Nakamura | G01R 33/283 378/4 |
| 2008/0183475 A1 | 7/2008 | Hirota et al. | |
| 2010/0142670 A1* | 6/2010 | Saito | A61B 6/032 378/8 |
| 2010/0246925 A1* | 9/2010 | Nagatsuka | A61B 5/1135 382/132 |

FOREIGN PATENT DOCUMENTS

| | | |
|---|---|---|
| JP | 2005312776 A | 11/2005 |
| JP | 2008-67935 A | 3/2006 |
| JP | 2010-046212 A | 3/2010 |

OTHER PUBLICATIONS

"RADspeed Pro EDGE package", available at: https://www.shimadzu.com/med/products/radio/m-od0gjn00000025sa.html, downloaded Feb. 17, 2021, this webpage or substantially similar webpage understood to have been available at least as of Jun. 11, 2018, submitted with a machine translation.

"Voice Generator Nice Call", available at: http://www.san-kyo.co.jp/products/%E3%83%8A%E3%82%A4%E3%82%B9%E3%82%B3%E3%83%BC%E3%83%AB/, downloaded Feb. 17, 2021, this webpage or substantially similar webpage understood to have been available at least as of Jun. 11, 2018, submitted with a machine translation.

"Medical Voice", available at:http://www.orrad.co.jp/product_medicalvoice.php, downloaded Feb. 17, 2021, this webpage or substantially similar webpage understood to have been available at least as of Jun. 11, 2018, submitted with a machine translation.

Katsuhara et al., "Dynamic Image Analysis in Dynamic Chest Radiography", Konica Minolta Technology Report vol. 15 (2018).

Yamada et al., "Difference in diaphragmatic motion during tidal breathing in astanding position between COPD patients and normal subjects: Time-resolved quantitative evaluation using dynamic chestradiography with flat panel detector system ("dynamic X-rayphrenicography")", European Journal of Radiology, 87 (2017) 76-82.

First Office Action dated Jan. 5, 2022 for corresponding Japanese Patent Application No. JP 2020-547664.

* cited by examiner

RADIOGRAPHIC IMAGING DEVICE

TECHNICAL FIELD

The present invention relates to a radiographic imaging device, such as, e.g., an X-ray imaging device, and more particularly to a radiographic imaging device equipped with a voice guidance function.

BACKGROUND ART

In a diagnostic X-ray imaging device for diagnosing a respiratory system of a subject, it is required to match the breathing timing of the subject with the X-ray imaging timing. For example, in chest radiography in which X-ray imaging is performed with the lungs inflated, it is required that the subject largely inhale and hold the inhaled state, and during the inhaled state, X-ray imaging is performed by irradiating X-rays. If the lungs move due to breathing during the X-ray irradiation, the captured X-ray image may be blurred, affecting the diagnostics.

For this reason, it has been proposed to output voice guidance at the time of X-ray imaging (see Patent Document 1 and Patent Document 2). A voice guidance device called "Auto Voice" is marketed to support the breath-holding timing of a subject. When this voice guidance device is used, the voice guidance device announces that "Please breathe and hold it" to a subject at the timing of pressing the X-ray preparation start switch of the X-ray imaging device, in conjunction with the imaging operation of the X-ray imaging device. Then, when the X-ray imaging switch of the X-ray imaging device is pressed, X-rays will be emitted from the X-ray imaging device, and an X-ray image will be acquired after completion of the X-ray irradiation. At the time of completion of this X-ray imaging, the voice guidance device announces, "Imaging has been completed".

In addition to general imaging in which single X-ray imaging is performed by performing X-ray irradiation only once when an X-ray imaging switch is pressed, in some cases, serial imaging (serial radiography) is performed in which a plurality of X-ray images is sequentially captured by performing a plurality of X-ray irradiation operations while the X-ray imaging switch is kept pressed. At the time of this serial imaging, for example, when the frame rate is 15 fps (frames per second), 225 times of X-ray imaging are performed in 15 seconds.

In the voice guidance at the time of this serial imaging, for example, in the period of five seconds after the X-ray imaging preparation button of the X-ray imaging device is first pressed, an announcement for instructing a subject to inhale is made by a voice guidance device. Next, in the period of two seconds from the depression of the X-ray imaging switch of the X-ray imaging device to the start of the X-ray imaging, an announcement for instructing the subject to hold the breath is made by the voice guidance device. Then, while continuing the successive X-ray imaging, in the period of the next five seconds, an announcement for instructing the subject to exhale is made by the voice guidance device. Thereafter, in the period of the next two seconds, an announcement for instructing the subject to hold the breath is made by the voice guidance device. Thereafter, in the period of the next five seconds, an announcement for instructing the subject to exhale is made by the voice guidance device. Then, the pressing of the X-ray imaging switch in the X-ray imaging device is released, and an announcement notifying that the imaging has been completed is made by the voice guidance device in the period of two seconds.

PRIOR ART DOCUMENT

Patent Document

Patent Document 1: Japanese Unexamined Patent Application Publication No. 2000-325339
Patent Document 2: Japanese Unexamined Patent Application Publication No. 2008-67935

SUMMARY OF THE INVENTION

Problems to be Solved by the Invention

In the case of serial imaging, unlike general imaging, it requires a subject to perform special breathing, and therefore it is preferable that the subject practice the breathing method before performing the imaging. At the time of this practice, a radiology technician or the like instructs a subject to the breathing method near the subject. At this time, by practicing the breathing method using the voice guidance device, which is to be actually used for serial imaging, it becomes possible to perform appropriate breathing without any difference between breathing at the actual imaging time and that at the practice time.

However, in order to operate the voice guidance device for the practice of the breathing method, preparation of X-ray imaging and irradiation of X-rays are performed in the X-ray imaging device. Therefore, in order to prevent radiation exposure of the subject or the like, there is a need to provide an exposure prevention means, such as, e.g., an X-ray protection lead screen.

Further, it is also possible to solve such a problem by preparing a voice guidance device that does not interlock with the X-ray imaging operation of the X-ray imaging device, apart from a normal voice guidance device. However, in this case, it is necessary to prepare two voice guidance devices, which is not only costly, but also it is necessary to secure a space for installing the devices.

The present invention has been made to solve the above problems, and it is an object of the present invention to provide a radiographic imaging device capable of performing a practice of a breathing method or the like using an existing voice guidance device without considering radiation exposure.

Means for Solving the Problem

According to a first aspect, an embodiment includes:
an imaging mechanism configured to perform radiographic imaging of a subject, the imaging mechanism being provided with a radiation irradiation unit and a radiation detection unit;
a voice guidance unit configured to output voice guidance to the subject; and
a control unit configured to switch between a practice mode for performing only the voice guidance by the voice guidance unit and an imaging mode for performing the radiographic imaging by the imaging mechanism in synchronization with the voice guidance by the voice guidance unit.

According to a second aspect, in an embodiment according to the first aspect, the imaging mechanism is capable of performing general imaging for capturing a single radiographic image and serial imaging for continuously capturing a plurality of radiographic images, and the control unit selects the imaging mode when performing the general imaging and selects either the practice mode or the imaging mode when performing the serial imaging.

According to a third aspect, in an embodiment according to the second aspect, the imaging mechanism is provided with a touch panel liquid crystal display unit, and the control unit displays a practice mode execution start switch on the touch panel liquid crystal display unit when performing the serial imaging.

According to a fourth aspect, in an embodiment according to the third aspect, the control unit displays the practice mode execution start switch on the touch panel liquid crystal display unit when performing the serial imaging and displays an imaging preparation switch when performing the general imaging on the touch panel liquid crystal display unit when performing the general imaging.

According to a fifth aspect, in an embodiment according to the second aspect, the imaging mechanism is provided with the practice mode execution start switch, and the control unit enables the practice mode execution start switch when performing the serial imaging and disables the practice mode execution start switch when performing the general imaging.

According to a sixth aspect, in an embodiment according to the second aspect, the imaging mechanism is provided with a preparation start switch for causing the imaging mechanism to start preparation of the radiographic imaging, and the control unit starts execution of the practice mode when the preparation start switch is operated when performing the serial imaging and causes the imaging mechanism to start preparation of the radiographic imaging when the preparation start switch is operated when performing the general imaging.

Effects of the Invention

According to the first aspect, it is possible to switch between the practice mode, which performs only voice guidance by the voice guidance unit, and the imaging mode, which performs radiographic imaging by the imaging mechanism in synchronization with the voice guidance by the voice guidance unit. Therefore, it is possible to execute a practice of a breathing method or the like using an existing voice guidance device without considering radiation exposure.

According to the second aspect, since the imaging mode is selected at the time of general imaging, which does not require a practice of a breathing method or the like, and the practice mode can be selected at the time of serial imaging, which requires a practice. Therefore, it is possible to select the mode of the voice guidance according to the imaging mode.

According to the third aspect, the practice mode can be easily started at the time of performing serial imaging.

According to the fourth aspect, the practice mode can be easily started when performing serial imaging, and the preparation for imaging can be easily started at the time of performing general imaging.

According to the fifth aspect, the practice mode can be easily started at the time of performing serial imaging, and a practice mode can be prevented from being executed at the time of performing general imaging.

According to the sixth aspect, by using the preparation start switch, the practice mode can be easily started at the time of performing serial imaging, and the preparation for imaging can be easily started at the time of performing general imaging.

EMBODIMENTS FOR CARRYING OUT THE INVENTION

Figure 1:
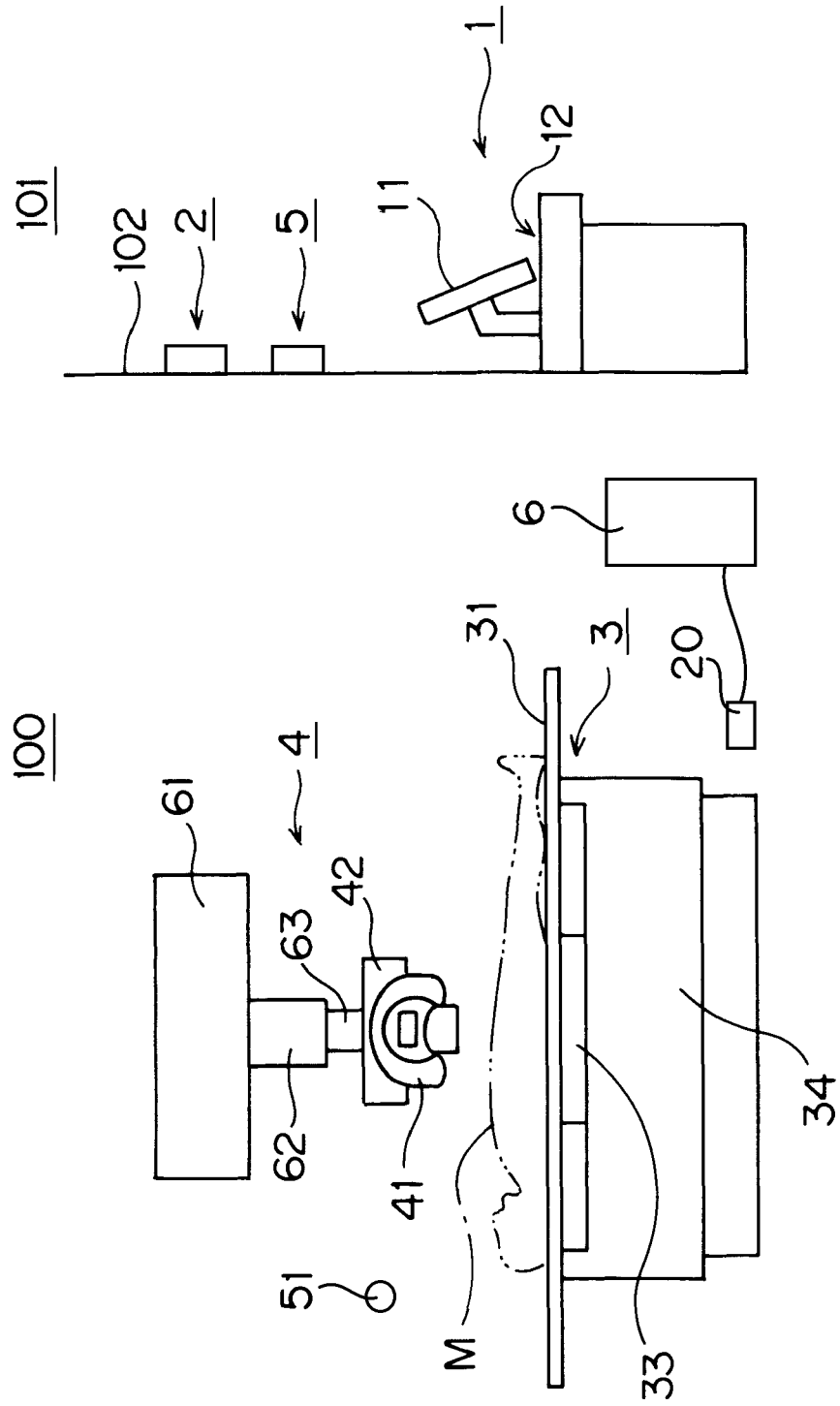
FIG. 1 is a schematic diagram of an X-ray imaging device according to the present invention.
Figure 2:
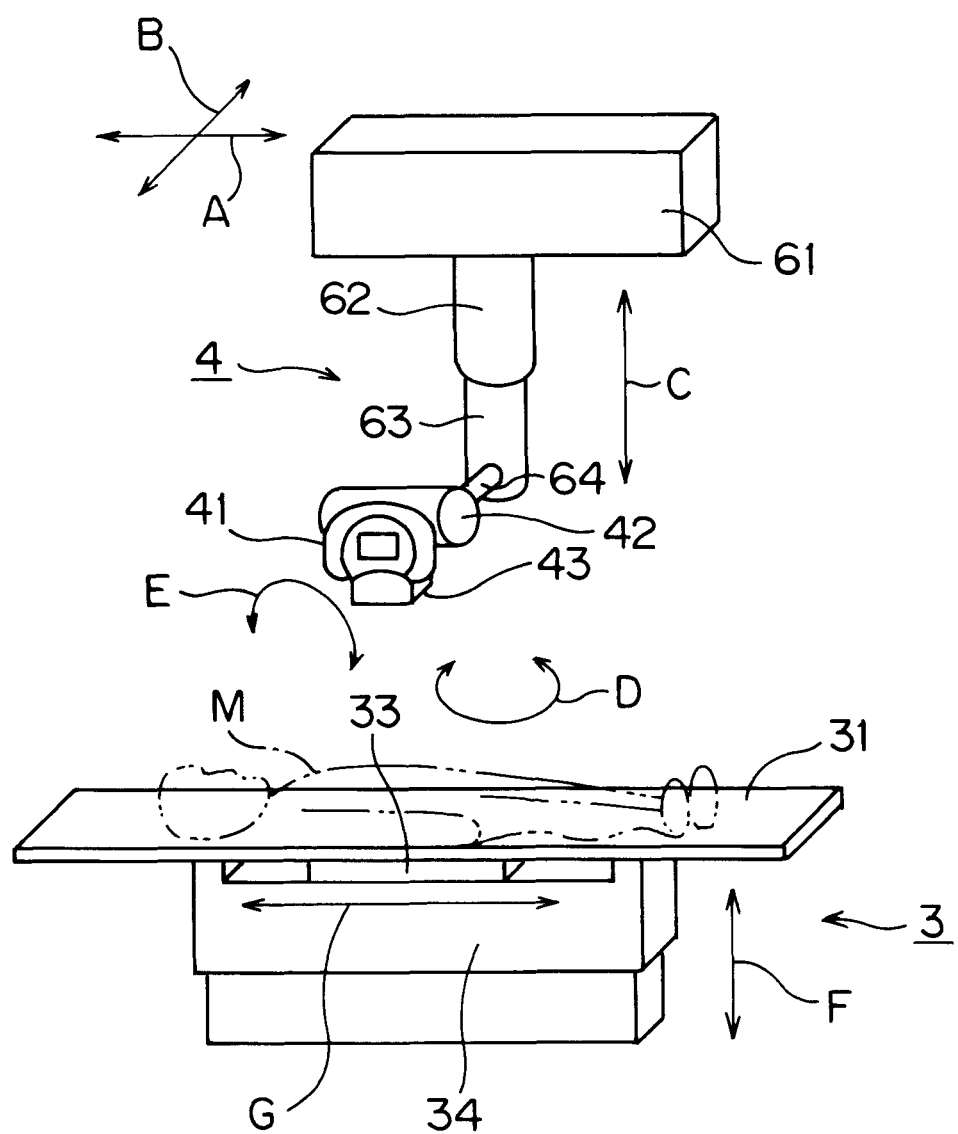
FIG. 2 is a perspective view of an examination table 3 and an imaging unit 4 in the X-ray imaging device according to the present invention.

Hereinafter, some embodiments of the present invention will be described with reference to the attached drawings. FIG. 1 is a schematic diagram of an X-ray imaging device as a radiation imaging device according to the present invention. FIG. 2 is a perspective view of an examination table 3 and an imaging unit 4 in the X-ray imaging device as the radiographic imaging device according to the present invention.

The X-ray imaging device according to the present invention is provided with a console unit 1, an operation unit 2, and a voice guidance unit 5, which are installed in an operation room 101 for an operator to execute X-ray imaging operations and the like, and an examination table 3 and an imaging unit 4, which are installed in an imaging room 100 for imaging a subject M. The imaging room 100 and the operation room 101 are shielded by a partition wall 102.

The console unit 1 installed in the operation room 101 is provided with a display unit 11 composed of a liquid crystal display and the like, and an operation unit 12 composed of a keyboard, a mouse, and the like, for performing various operations. The X-ray images and the like are displayed on the display unit 11. The console unit 1 is connected to an in-hospital network, which is an in-hospital communication of a subject management system in a hospital (not shown).

The voice guidance unit 5 provided in the operation room 101 is composed of a commercially available voice guidance device called "Auto Voice." The voice guidance unit 5 is for generating voice guidance for supporting the breath holding timing of a subject M and is connected to a speaker 51 installed on a wall or the like of the imaging room 100.

Figure 3:
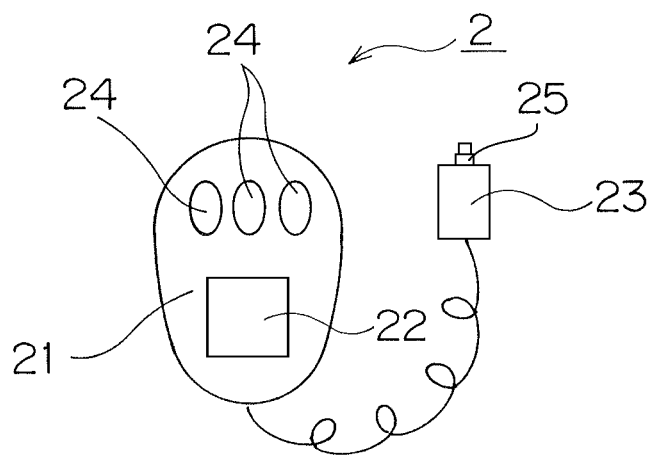
FIG. 3 is a schematic diagram of an operation unit 2.

FIG. 3 is a schematic diagram of the operation unit 2.
The operation unit 2 is mounted on the partition wall 102 in the operation room 101. The operation unit 2 is equipped with an operation panel 21 including a touch panel liquid crystal display unit 22 and input buttons 24, and a hand switch 23 including a two-stage push-button 25 for transmitting signals for X-ray irradiation and its preparation for the X-ray tube 42 in the imaging unit 4. The operation unit 2 is for setting the tube voltage and the tube current of the X-ray tube 42, or for setting the X-ray irradiation conditions, such as, e.g., an X-ray irradiation time. This operation unit 2 is connected to a high-voltage generation unit 6 disposed in the imaging room 100. This high-voltage generation unit 6 provides a high voltage to the X-ray tube 42 to allow X-ray irradiation. Note that the high-voltage generation unit 6 is connected to a footswitch 20 used to start X-ray irradiation in the imaging room 100.

Referring again to FIG. 1 and FIG. 2, the examination table 3 is provided with a top board 31 for placing a subject M thereon, an X-ray detection unit 33 in which a flat panel detector (FPD) as an X-ray detector is housed, and a lifting and lowering unit 34 for lifting and lowering the top board 31 and the X-ray detection unit 33. The X-ray detection unit 33 is horizontally movable in the G-direction shown in FIG. 2. Further, the X-ray detection unit 33 can be lifted and lowered together with the top board 31 in the F-direction shown in FIG. 2.

As shown in FIG. 2, the imaging unit 4 is provided with a base 61 movable in the A-direction and the B-direction perpendicular to each other with respect to the ceiling of the imaging room 100, a support portion 62 extending downward from the base 61, a moving unit 63 which is raised and lowered with respect to the support portion 62 in the C-direction and is rotatable in the D-direction, and a support shaft 64 rotatably supported at the lower end of the moving unit 63 to integrally rotate the handle 45, the X-ray tube 42, and the collimator 43 in the E-direction. Therefore, the handle 45, the X-ray tube 42, and the collimator 43 are movable in the A-direction, the B-direction, the C-direction, the D-direction, and the E-direction.

Figure 4:
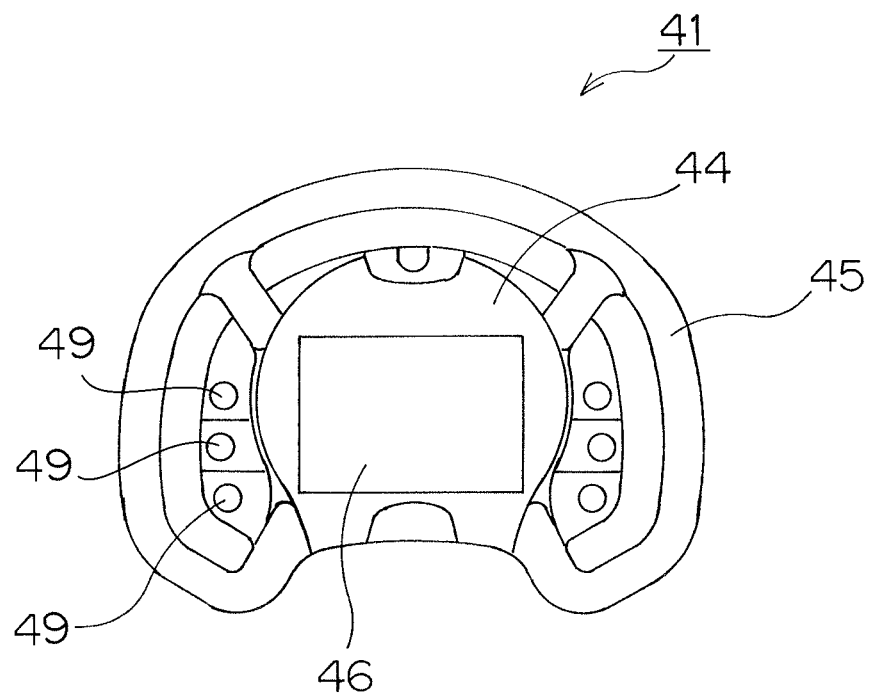
FIG. 4 is a diagram showing a front view of an operation unit 41 in the imaging unit 4.

FIG. 4 is a front view of the operation unit 41 in the imaging unit 4.

The operation unit 41 is composed of a handle 45 for moving the X-ray tube 42 together with the collimator 43 and an operation panel 44. At the center of the operation panel 44, a touch panel liquid crystal display unit 46 is provided. A plurality of input buttons 49 is provided around the liquid crystal display unit 46.

Figure 5:
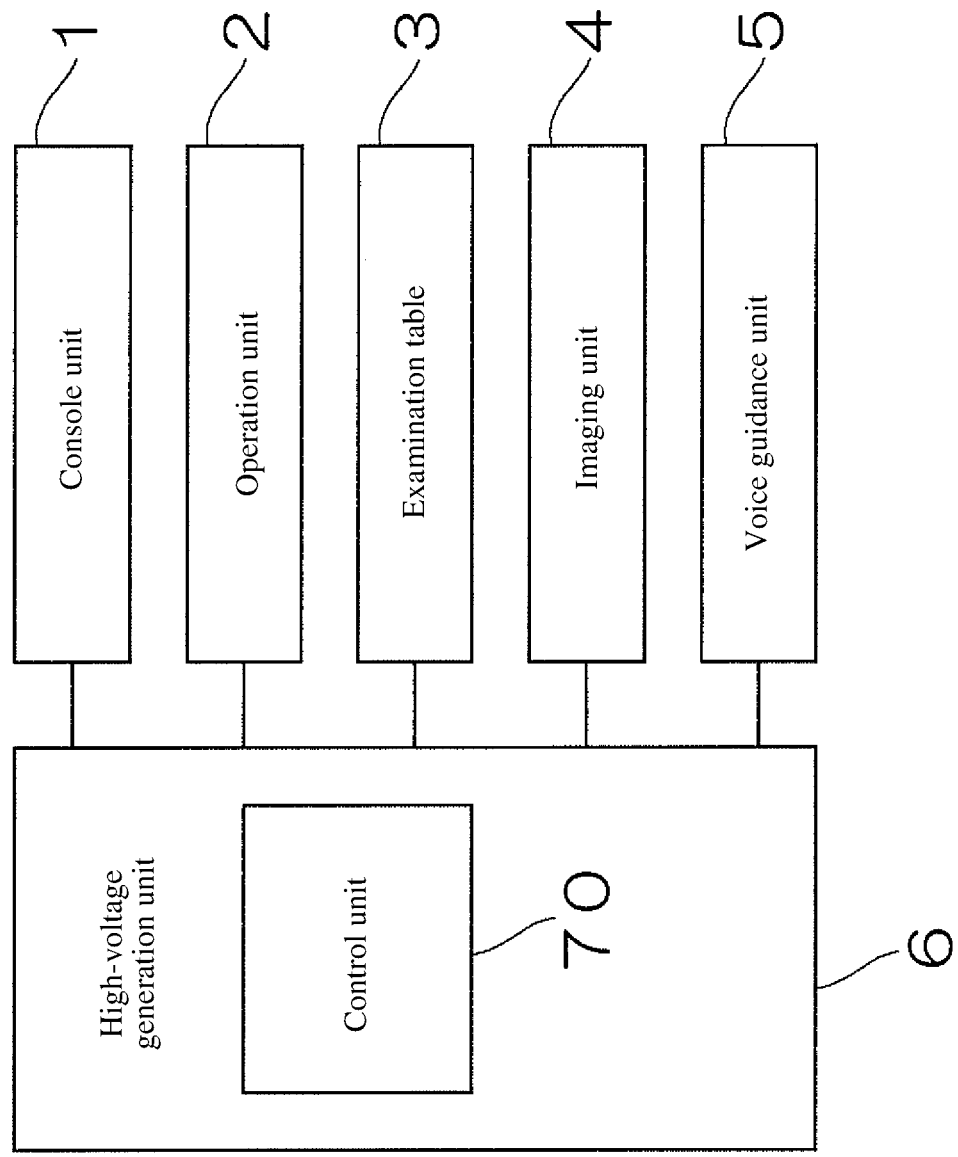
FIG. 5 is a block diagram showing a main control system of the X-ray imaging device.

FIG. 5 is a block diagram showing the main control system of the X-ray imaging device as the radiographic imaging device according to the present invention.

In the high-voltage generation unit 6, a control unit 70 for controlling the entire device is provided. The control unit 70 is configured by a computer with software installed. The various functions included in this control unit 70 are realized by performing the software installed in a computer. The control unit 70 in the high-voltage generation unit 6 is connected to the console unit 1, the operation unit 2, the examination table 3, the imaging unit 4, and the voice guidance unit 5 described above.

Note that in the embodiment shown in FIG. 5, it is described that the control unit 70 is provided in the high-voltage generation unit 6. However, the control unit 70 may be provided in a member, such as, e.g., the console unit 1, other than the high-voltage generation unit 6. Further, the function may be divided and provided in a plurality of members. Further note that in the embodiment shown in FIG. 5, the console unit 1, the operation unit 2, the examination table 3, the imaging unit 4, and the voice guidance unit 5 are connected via the high-voltage generation unit 6, but these units/table may be connected to each other in any form.

This X-ray imaging device is capable of performing general imaging for capturing a single radiographic image and serial imaging for consecutively capturing a plurality of images as the operation of the imaging mechanism composed of the console unit 1, the operation unit 2, the examination table 3, the imaging unit 4, and the high-voltage generation unit 6. Whether to perform either the general imaging or the serial imaging can be selected from the operation unit 12 of the console unit 1, the operation unit 2, or the operation unit 41 of the imaging unit 4. Further, the voice guidance unit 5 in the X-ray imaging device is switchable between a practice mode that performs only the voice guidance and an imaging mode that performs the X-ray imaging by the imaging mechanism in synchronization with the voice guidance. The above-described control unit 70 selects the imaging mode at the time of performing general imaging and selects either the practice mode or the imaging mode at the time of performing the serial imaging.

Figure 6:
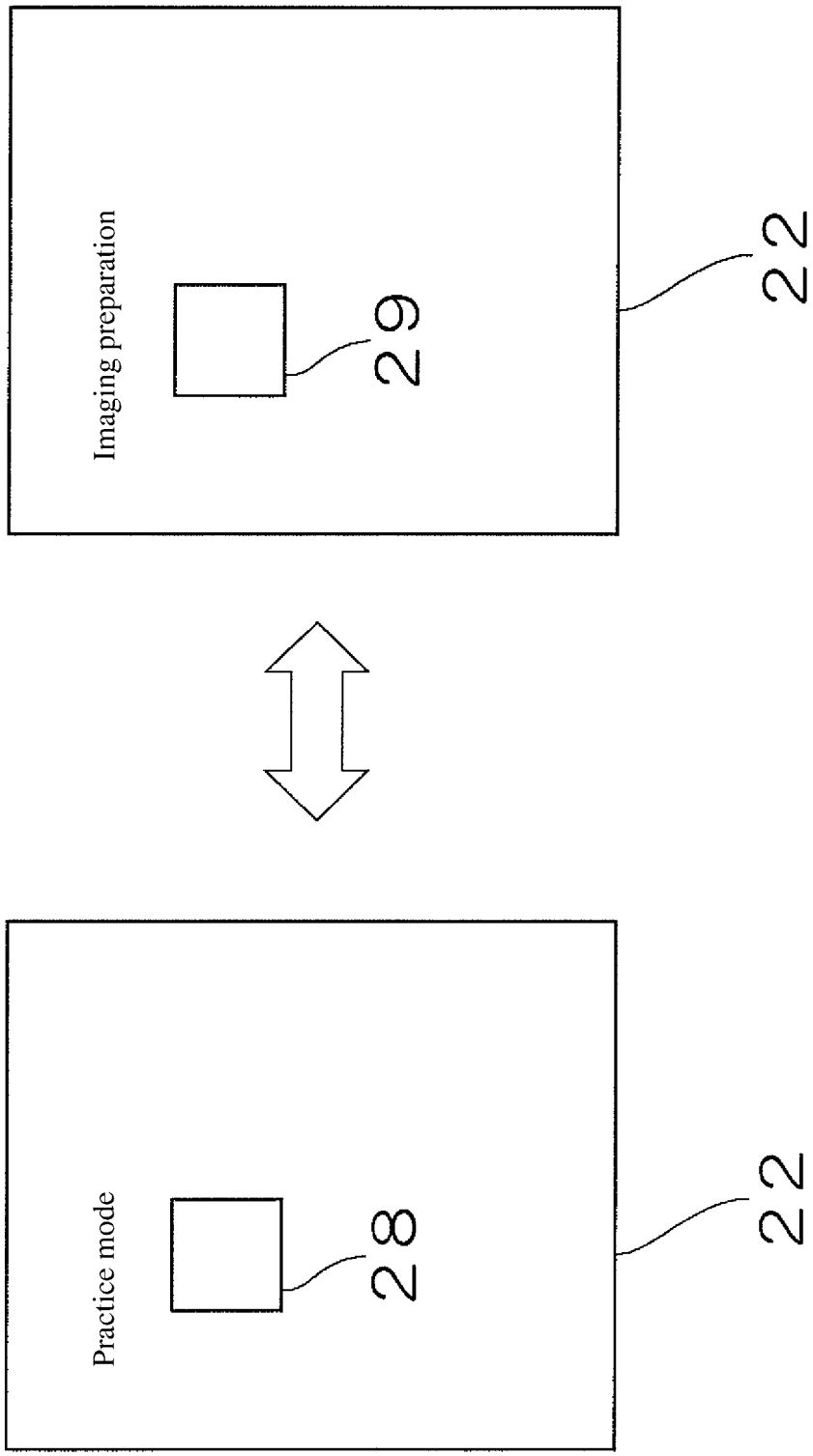
FIG. 6 is a schematic diagram showing an example of a display screen of a touch panel liquid crystal display unit 22 in the operation unit 2.

FIG. 6 is a schematic diagram showing an example of a display screen of the touch panel liquid crystal display unit 22 in the operation unit 2.

When performing serial imaging, the control unit 70 displays the practice mode execution start switch 28 on the touch panel liquid crystal display unit 22. When this practice mode execution start switch 28 is operated, the practice mode that performs only the voice guidance by the voice guidance unit 5 is executed. Further, when performing general imaging, the control unit 70 displays the imaging preparation switch 29 when performing general imaging on the touch panel liquid crystal display unit 22. When this imaging preparation switch 29 is pressed, the rotating anode in the X-ray tube 42 starts rotating as a preliminary operation of the X-ray tube 42 before performing general imaging, and performs the preparation of X-ray irradiation. Note that the practice mode execution start switch 28 or the imaging preparation switch 29 is also displayed on the touch panel liquid crystal display unit 46 in the operation unit 41 of the imaging unit 4.

When the operator operates the operation unit 12 of the console unit 1, the operation unit 2, or the operation unit 41 of the imaging unit 4 of the operation unit 41 to select general imaging, as shown on the right in FIG. 6, the imaging preparation switch 29 at the time of general imaging is displayed on the touch panel liquid crystal display unit 22 in the operation unit 2. When the operator presses this imaging preparation switch 29, the rotating anode in the X-ray tube 42 starts rotating as a preliminary operation of the X-ray tube 42 before performing general imaging to start the preparation of X-ray irradiation. Thereafter, general imaging is performed when the operator presses the pushbutton 25 in the hand switch 23 of the operation unit 2.

On the other hand, when the operator operates the operation unit 12 of the console unit 1, the operation unit 2, or the operation unit 41 of the imaging unit 4 to select serial imaging, the practice mode execution start switch 28 is displayed on the touch panel liquid crystal display unit 22 in the operation unit 2 as shown on the left side in FIG. 6. When the operator presses the practice mode execution start switch 28, the control unit 70 shown in FIG. 5 starts the practice mode for performing only the voice guidance by the voice guidance unit 5. On the other hand, when the operator did not press the practice mode execution start switch 28, the control unit 70 shown in FIG. 5 starts the imaging mode for performing X-ray imaging by the imaging mechanism in synchronization with the voice guidance by the voice guidance unit 5 according to the following operation by the operator.

Figure 7:
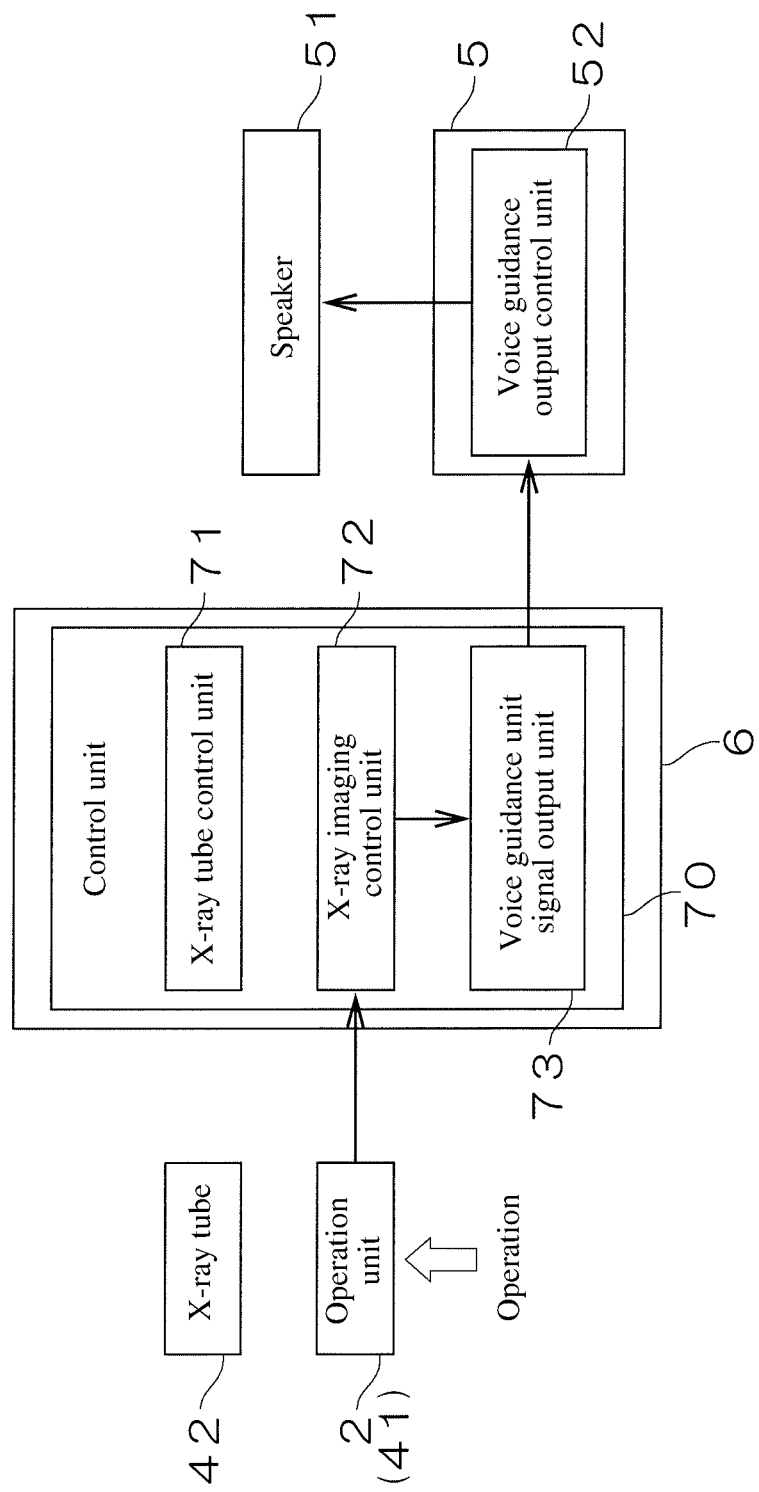
FIG. 7 is a block diagram showing a transmission status of a command signal at the time of the practice mode.
Figure 8:
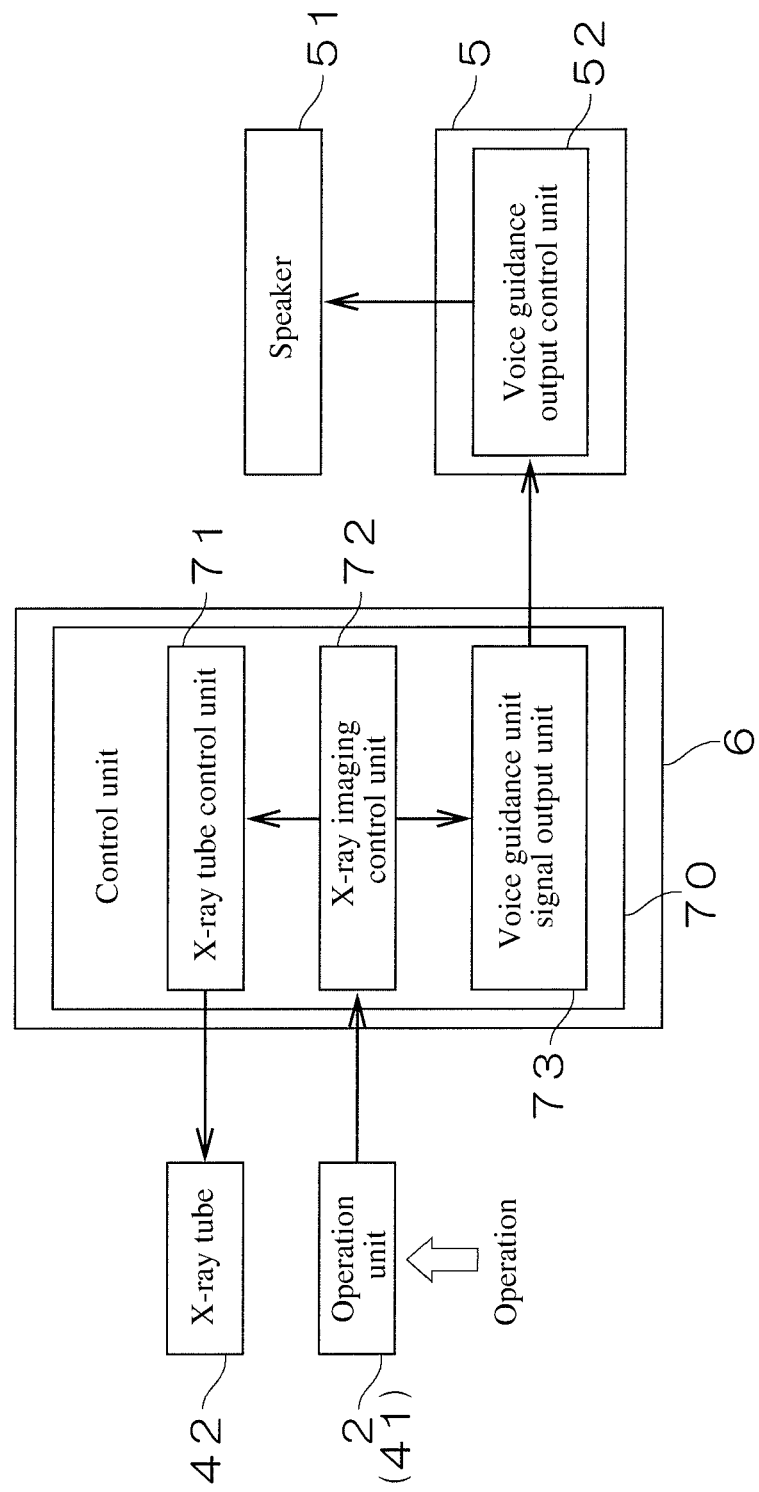
FIG. 8 is a block diagram showing a transmission state of a command signal at the time of the imaging mode.

FIG. 7 is a block diagram showing a transmission state of a command signal at the time of the practice mode in which only the voice guidance by the voice guidance unit 5 is executed, and X-ray imaging by the imaging mechanism is not performed. FIG. 8 is a block diagram showing a transmission state of a command signal at the time of the imaging mode in which X-ray imaging by the imaging mechanism is performed in synchronization with the voice guidance by the voice guidance unit 5.

After the operator presses the practice mode execution start switch 28 displayed on the touch panel liquid crystal display unit 22 in the operation unit 2 or the touch panel liquid crystal display unit 46 in the operation unit 41 in the imaging unit 4 and the mode has been shifted to the practice move, when the operation unit 2 or the operation unit 41 in the imaging unit 4 is operated as shown in FIG. 7, the signal from the X-ray imaging control unit 72 is transmitted to the voice guidance output control unit 52 in the voice guidance unit 5 via the voice guidance unit signal output unit 73. The voice guidance output control unit 52 in the voice guidance unit 5 transmits a signal for outputting voice guidance to the speaker 51. As a result, the same voice as the voice when performing serial imaging is output from the speaker 51, and that the subject M can execute the practice of a breathing method or the like. At this time, since no X-rays are irradiated from the X-ray tube 42, no consideration of X-ray exposure is required.

In cases where the operator operates the operation unit 41 of the imaging unit 4 to shift the mode to the practice mode and operates the operation unit 41 of the imaging unit 4 to execute the practice of a subject M, it is possible to eliminate the need for the operator to move between the imaging room 100 and the operation room 101 when the operator performs the practice beside the subject M.

On the other hand, when the operator operates the operation unit 2 or the operation unit 41 of the imaging unit 4 without shifting the mode to the practice mode, as shown in FIG. 8, the signal from the X-ray imaging control unit 72 is transmitted to the voice guidance unit signal output unit 73 and the X-ray tube control unit 71. Then, from the voice guidance unit signal output unit 73, a signal is transmitted to the voice guidance output control unit 52 in the voice guidance unit 5, and the voice guidance output control unit 52 in the voice guidance unit 5 transmits a signal for outputting voice guidance to the speaker 51. Further, an X-ray irradiation signal is transmitted from the X-ray tube control unit 71 to the X-ray tube 42. As a result, voice guidance corresponding to each step of serial imaging is output from the speaker 51, and serial imaging is performed for the subject M who breathes by the breathing method which has been practiced in advance.

In the embodiment described above, the practice mode execution start switch 28 is displayed on the touch panel liquid crystal display unit 22, 46 when performing serial imaging, and the imaging preparation switch 29 when performing general imaging is displayed on the touch panel liquid crystal display unit 22, 46 when performing general imaging 29. The practice mode is executed by pressing the practice mode execution start switch 28. However, other methods may be used as a configuration for initiating the practice mode.

That is, as a first modification for initiating the practice mode, any one of the plurality of input buttons 24 in the operation unit 2 or any one of the plurality of input buttons 49 in the operation unit 41 of the imaging unit 4 is set as an execution start switch. When performing serial imaging, this practice mode execution start switch is enabled by the control unit 70, while when performing normal imaging, the practice mode execution start switch is disabled by the control unit 70. This can prevent the mode from becoming the practice mode at the time of general imaging.

Further, as a second modification for initiating the practice mode, the first stage of the two-stage push-button 25 in the hand switch 23 of the operation unit 2 is set as the preparation start switch of the X-ray imaging when performing general imaging and set as the practice mode execution start switch when performing serial imaging. Even when such a configuration is adopted, this can be prevented the mode from becoming the practice mode at the time of general imaging.

Note that in the embodiments described above, the practice mode is started by using any one of the console unit 1, the operation unit 2, the examination table 3, the imaging unit 4, and the high-voltage generation unit 6. However, separately from the imaging mechanism, a dedicated practice operation unit for performing the practice mode may be provided. In this case, the practice operation unit may be attached to somewhere in the imaging mechanism or may be provided independently of the imaging mechanism. The signal transmission and reception between the practice operation unit and the imaging mechanism or the voice guidance unit 5 may be performed by wired communication or may be performed by wireless communication.

DESCRIPTION OF SYMBOLS

1: Console unit
2: Operation unit
3: Examination table
4: Imaging unit
5: Voice guidance Department
6: High-voltage generation unit
11: Display unit
12: Operation unit
20: Footswitch
21: Operation panel
22: Touch panel liquid crystal display unit
23: Hand switch
24: Input button
27: Switch unit
28: Practice mode execution start switch
29 Imaging preparation switch when performing general imaging
31: Top board
33: X-ray detection unit
41: Operation unit
42: X-ray tube
43: Collimator
45: Handle
46: Touch panel liquid crystal display unit
49: Input button
51: Speaker
52: Voice guidance output control unit
70: Control unit
71: X-ray tube control unit
72; X-ray imaging control unit
73: Signal output unit for a voice guidance unit
74: Set time storage unit
100: Imaging room
101: Operation room
M Subject

The invention claimed is:
1. A radiographic imaging device comprising:
an imaging mechanism configured to perform serial imaging in which a plurality of radiographic images of a subject are consecutively captured and general imaging in which a single radiographic image of the subject is captured, the imaging mechanism being provided with a radiation irradiation unit and a radiation detection unit;

a voice guidance unit configured to output voice guidance to the subject;

a controller configured to switch between a practice mode in which only the voice guidance by the voice guidance unit is performed and an imaging mode in which radiographic imaging is performed by the imaging mechanism in synchronization with the voice guidance by the voice guidance unit; and an operation unit configured to receive an input operation of selecting either the practice mode or the imaging mode, wherein the controller is configured to perform one of the practice mode and the imaging mode according to the input operation received by the operation unit when performing the serial imaging and perform the imaging mode with disabling of the practice mode when performing the general imaging.

2. The radiographic imaging device as recited in claim 1, wherein the imaging mechanism is provided with a touch panel display unit, and wherein the controller is configured to display a practice mode execution start switch on the display unit when performing the serial imaging.

3. The radiographic imaging device as recited in claim 2, wherein the controller is configured to display an imaging preparation switch when performing the general imaging on the display unit when performing the general imaging.

4. The radiographic imaging device as recited in claim 1, wherein the imaging mechanism is provided with a practice mode execution start switch, and wherein the controller is configured to enable the practice mode execution start switch when performing the serial imaging and disables the practice mode execution start switch when performing the general imaging.

5. The radiographic imaging device as recited in claim 1, wherein the imaging mechanism is provided with a preparation start switch for causing the imaging mechanism to start preparation of the radiographic imaging, and wherein the controller is configured to start execution of the practice mode when the preparation start switch is operated when performing the serial imaging and causes the imaging mechanism to start preparation of the radiographic imaging when the preparation start switch is operated when performing the general imaging.

* * * * *